US006451730B1

(12) United States Patent
Friedrich et al.

(10) Patent No.: US 6,451,730 B1
(45) Date of Patent: Sep. 17, 2002

(54) TWO-STAGE PREPARATION OF PROMOTED V/SB-OXIDE AMMOXIDATION CATALYSTS

(75) Inventors: Maria Strada Friedrich, Lyndhurst; Michael J. Seely, Twinsburg; Dev Dhanaraj Suresh, Hudson, all of OH (US)

(73) Assignee: The Standard Oil Company, Chicago, IL (US)

( * ) Notice: Subject to any disclaimer, the term of this patent is extended or adjusted under 35 U.S.C. 154(b) by 624 days.

(21) Appl. No.: 08/883,716

(22) Filed: Jun. 27, 1997

(51) Int. Cl.⁷ .............................. B01J 23/70; B01J 23/00
(52) U.S. Cl. ........................ 502/338; 502/350; 502/352
(58) Field of Search .................................. 502/338, 350, 502/352, 353

(56) References Cited

U.S. PATENT DOCUMENTS 5,214,016 A * 5/1993 Brazdil et al. ............... 502/202
5,498,588 A * 3/1996 Brazdil et al. ............... 502/353

* cited by examiner

*Primary Examiner*—T A Solola
*Assistant Examiner*—Joseph Murray
(74) *Attorney, Agent, or Firm*—David P. Yusko

(57) ABSTRACT

A process for the preparation of a promoted $VSbO_x$ catalyst comprising mixing a vanadium compound, at least a first portion of an antimony compound, and at least a portion of the support material to form a slurry, heating the slurry to remove the water, calcining the dried slurry to form a catalyst precursor, combining the catalyst precursor with a second aqueous sol containing the remaining portion of the support material and the remaining portion of the antimony compound to form a second slurry, drying the second slurry to remove the water and calcining the dried mixture to form the finished catalyst.

13 Claims, No Drawings

TWO-STAGE PREPARATION OF PROMOTED V/SB-OXIDE AMMOXIDATION CATALYSTS

BACKGROUND OF THE INVENTION

Field of the Invention

The present invention is directed to a method for the preparation of promoted $VSbO_x$ based catalyst useful in the catalytic vapor phase ammoxidation of propylene or isobutylene to acrylonitrile or methacrylonitrile. In addition, the present invention is directed to a method for catalytic vapor phase ammoxidation of propylene or isobutylene to acrylonitrile or methacrylonitrile in a fluid bed reactor by contacting with a fluid bed ammoxidation catalyst made by the process of the present invention.

U.S. Pat. No. 4,162,992 discloses the ammoxidation of olefins, especially propylene, using a catalyst containing vanadium, antimony and titanium. However, the amount of antimony is far outside the range of the catalyst made by the present claimed process.

In U.S. Pat. No. 3,681,421 to Barclay et al there is disclosed the vapor phase catalytic ammoxidation of propylene over an oxide composition comprising antimony, vanadium and one or more additional poly-valent metals selected from the group of tin, iron, cobalt and titanium. The catalyst disclosed by Barclay et al overlap with the empirical formula of the compositions of the catalyst of the present invention. However, the catalyst of the present invention are made by a different method than the catalyst disclosed by Barclay et al.

Finally, in U.S. Pat. No. 5,258,543 to Suresh et al, assigned to the assignee of the instant application, there is disclosed a suitable procedure for making a $VSbO_x$ promoted catalyst useful in the ammoxidation of propylene to acrylonitrile. The present invention is directed to an improvement in the procedure for making the $VSbO_x$ promoted catalyst of the U.S. Pat. No. 5,258,543. The properties of the catalyst prepared by the present invention have superior properties than those disclosed in the prior art.

SUMMARY OF THE INVENTION

It is the primary object of the present invention to provide a novel process for the preparation of promoted $VSbO_x$ based catalyst useful in the ammoxidation of propylene or isobutylene to produce acrylonitrile or methacrylonitrile.

It is another object of the present invention to provide a novel procedure for the catalytic vapor phase ammoxidation of propylene or propane to acrylonitrile or methacrylonitrile.

Additional objects, advantages and novel features of the invention, will be set forth in part in the description which follows, and, in part, will become apparent to those skilled in the art upon examination of the following or may be learned by the practice of the invention. The objects and advantages of the invention may be realized and attained by means of the instrumentalities and combinations particularly pointed out in the appended claims.

To achieve the foregoing and other objects and in accordance with the purpose of the present invention as embodied and broadly described herein, the process of the present invention comprises preparing a supported catalyst wherein said catalyst comprises the elements and proportions indicated by the following empirical formula:

$$V_{1.0}Sb_aM_bO_x$$

wherein

M equals Sn, Ti, Fe, Cu, Nb, Ta, Co, Ni, Mg, Li, Na, Ga and mixtures thereof, a is from about 0.5 to about 5.0, b is from about 0.1 to 5.0, and x is the number of oxygen atoms required to satisfy the valency requirement of the other elements, comprising (1) mixing the vanadium compound, at least a portion of the antimony compound, at least a portion of the M compound and an aqueous sol containing a portion of the support material to form an aqueous slurry, heating the slurry to remove the water, and calcining at a temperature of at least about 150° C. to form a catalyst precursor; (2) mixing the catalyst precursor with an aqueous sol containing the remaining portion of the support material and any remaining portion of the antimony and M compounds to form a second slurry, (3) drying the second slurry to remove the water to form a dry mixture, and (4) calcining the dried mixture at a temperature of at least 150° C. to form the finished catalyst.

In a preferred embodiment of the present invention the portion of the support material added during the formation of the catalyst precursor is between 1 to 79% of the total amount of support material present in the finished catalyst.

In a further preferred embodiment of the present invention the remaining portion of support material present in the aqueous sol to which the catalyst precursor is mixed is between 1 to 79% of the total amount of support material present in the finished catalyst.

In still another preferred embodiment of the present invention all of the antimony compound is added during the formation of the catalyst precursor.

In still a further preferred embodiment of the present invention all of the M compound is added during the formation of the catalyst precursor.

In another further preferred embodiment of the present invention the catalyst precursor is calcined at a temperature of between about 150° to about 900° C., preferably between about 250° to 800° C., especially preferred being between about 300° to about 600° C.

In another preferred embodiment of the present invention the support material is selected from the group consisting of silica, alumina, titanium, zirconia, and mixtures thereof.

In a still further preferred embodiment of the present invention, the process further comprises forming the first aqueous slurry by mixing an aqueous dispersion containing the vanadium compound and at least a portion of the antimony compound while the vanadium is in solution prior to calcining to form the catalyst precursor.

In accordance with additional aspects of the present invention as embodied and broadly described herein, the method of manufacture of acrylonitrile or methacrylonitrile from propylene or isobutylene comprises introducing in the vapor state a hydrocarbon selected from the group consisting of propylene and propane, an oxygen-containing gas and ammonia into a fluid bed reactor containing an ammoxidation catalyst, wherein the catalyst contains elements in proportions indicated in the empirical formula set forth above. Wherein the catalyst is prepared by a process comprising (1) mixing the vanadium compounds, at least a portion of the antimony compound, at least a portion of the M compound and an aqueous sol containing a portion of the support material to form an aqueous slurry, heating the slurry to remove the water, and calcining at a temperature of at least about 150° C. to form a catalyst precursor; (2) mixing the catalyst precursor with an aqueous sol containing the remaining portion of the catalyst and any remaining portion of the antimony and M compounds to form a second slurry, (3) drying the second slurry to remove the water to form a dry mixture, and (4) calcining the dried mixture at a temperature of at least 150° C. to form the finished catalyst.

In a preferred embodiment of this aspect of the present invention the olefin is selected to be propylene.

In a still further preferred embodiment of this aspect of the present invention the olefin is selected to be isobutylene.

DETAILED DESCRIPTION OF THE INVENTION

The present invention is directed to a method of preparing a supported catalyst useful in the ammoxidation of acrylonitrile or methacrylonitrile. The catalyst comprises the elements in proportions indicated by the following empirical formula:

$$V_{1.0}Sb_aM_bO_x$$

wherein
M equals Sn, Ti, Fe, Cu, Nb, Ta, Co, Ni, Mg, Li, Na, Ga and mixtures thereof,
a is from about 0.5 to about 5.0,
b is from about 0.1 to 5.0, and
x is the number of oxygen atoms required to satisfy the valency requirement of the other elements.

The process of preparing the above-identified catalyst comprises mixing the vanadium compound, at least a portion of the antimony compound, at least a portion of the M compound in an aqueous sol containing a portion of the support material to form an aqueous slurry, heating the slurry to remove the water and calcining in a temperature of at least about 150° C. to form a catalyst precursor; (2) mixing the catalyst precursor with aqueous sol containing the remaining portion of the support for the catalyst and any remaining portion of the antimony and M compounds to form a second slurry; (3) drying the second slurry to remove the water to form a dry mixture, and calcining the dried mixture at a temperature of at least 150° C. to form the finished catalyst.

In particular, the catalyst precursor is made by the process disclosed in U.S. Pat. No. 5,258,543 assigned to the assignee of the present invention and herein incorporated by reference. In general, the catalyst precursor comprising vanadium antimony promoted oxide is made by adding the vanadium pentoxide to water containing hydrogen peroxide and stirring until a dark red peroxide complex has been formed. At least a portion of the antimony compound, preferably all the antimony compound, is then added to the slurry and the slurry is heated with the color in the slurry generally changing from yellow to green to black. The mixture is digested for approximately 3 hours while adding water to keep the volume constant. At least a portion of the M compound is added in the form of the water soluble salt, e.g. (metal salt) followed by the addition of at least a portion of the support material in the form of aqueous sol. The slurry is then evaporated on a hot plate at approximately a temperature of 120° C. and then calcined at a temperature of at least 150° C., preferably between 600° to 900° C., most preferably above 750° C. to form the catalyst precursor. For details with regard to the formation of the catalyst precursor, reference is made to U.S. Pat. No. 5,258,543 assigned to the assignee of the present invention and herein incorporated by reference.

The catalyst precursor made by the above procedure is then added to an aqueous sol containing the remaining portion of the support for the catalyst and any remaining portion of the antimony and M compounds. Typically, the antimony compound in the form of antimony oxide or the M compound in the form of a metal salt is simply mixed with the aqueous sol containing the remaining portion of the support for the catalyst prior to mixing with the catalyst precursor.

In the preferred embodiments of the present invention, Support material is selected from the group consisting of silica, alumina titanium, zirconium, and mixtures thereof. It is especially preferred that an aqueous sol of silica be used. Typical sources of silica useful in the practice of the present invention can be obtained from the Nalco Chemical Company of Chicago, Ill.

The catalyst prepared by the process of the present invention has particular utility in the ammoxidation of propylene and isobutylene to the corresponding α,β monounsaturated nitrile. The process comprises introducing the hydrocarbon, an oxygen-containing gas and ammonia into a reactor containing the ammoxidation catalyst prepared by the procedure of the present invention wherein the catalyst contains the elements in proportions indicated in the empirical formula set forth below:

$$V1.0Sb_aM_bO_x$$

wherein
M equals Sn, Ti, Fe, Cu, Nb, Ta, Co, Ni, Mg, Li, Na, Ga and mixtures thereof,
a is from about 0.5 to about 5.0,
b is from about 0.1 to 5.0, and
x is the number of oxygen atoms required to satisfy the valency requirement of the other elements.

Typically, the ammoxidation reaction is carried out in the temperature ranging from 350° to 700° C., preferably in the range of 430° to 520° C. Moreover, the reaction is carried out in the gaseous phase by contacting the mixture of the olefin, ammonia, molecular oxygen (oxygen containing gas) and an inert diluent, if any, in either a fixed bed, fluid bed, or fast transport reactor. In the preferred embodiment of the present invention, a fluid bed reactor is used.

Examples of applicable inert gaseous diluents are nitrogen, helium, carbon dioxide and water. In the process of the present invention the volume ratio of inert gaseous diluents to olefin fed to the reaction zone is usually in the range of 0 to 8, more often 0 to 4.

The average contact time can be from 0.01 to 10 seconds but is usually from 0.02 to 5 seconds, especially preferred being 0.1 to 2 seconds.

The pressure in the reaction zone usually ranges from just over atmospheric to up to 75 atmospheres, especially preferred being up to 50 psia.

The catalyst prepared by the process of the present invention similarly to the catalyst prepared in U.S. Pat. No. 5,258,543 have outstanding characteristics as propylene ammoxidation catalysts with acrylonitrile yields similar to those obtained with present day commercial amtimonate catalysts. The promoted catalysts of the present invention have significant potential as high throughput catalysts which give low levels of waste organics during use. A significant advantage of the catalyst prepared by the process of the present invention is that the process of the present invention allows for significantly easier preparation of the catalyst, along with increasing the hardness of the catalyst, which will result in additional or improved attrition resistance when used in the fluid bed reactor.

The following examples set forth below are illustrated by the present invention and the improved attrition resistance of the catalyst.

Catalyst Preparation

COMPARATIVE EXAMPLES 1 TO 5

Example 1

Catalyst No. 17147-92B
($V_{1.0}Sb_{1.2}Sn_{0.5}Ti_{1.0}Fe_{0.08}O_x$)

A catalyst having the above composition was prepared as follows: The $V_2O_5$ was added to a mixture of 900 cc distilled water and 100 g 30% $H_2O_2$. The mixture was stirred at RT~15 minutes, until a dark red peroxy complex solution was formed. $Sb_2O_3$ powder was added, and the mixture was refluxed for about 2.5 to 3.0 hours. The color of the slurry went from yellow to green to black. Water was added as needed, to keep the level constant. After the slurry passed the filter paper test (i.e., when a drop is placed on a filter paper, the black color does not bleed), the tin sol, fumed titania, iron acetate and silica sol were added. The slurry was evaporated on the hot plate and dried at 120° C. overnight. The catalyst was calcined at 290° C. for 3 hours, 425° C. for 3 hours, 650° C. for 8 hours, was ground and screened to a 20 to 35 mesh size. The catalyst was then calcined further at 900° C. for 3 hours.

Example 2

Catalyst No. 17173-15 ($V_{1.0}Sb_{1.2}Sn_{0.5}Ti_{1.0}Fe_{0.08}O_x$)

The procedure set forth in Example 1 was repeated to insure reproducibility of results.

Example 3

Catalyst No. 17173-16 ($V_{1.0}Sb_{1.2}Sn_{0.5}Ti_{1.0}Fe_{0.08}O_x$)

Repeat of Example 2, except that the fumed titania was added in the beginning, a few minutes after the antimony oxide was added.

Example 4

Catalyst No. 17173-17 ($V_{1.0}Sb_{1.2}Sn_{0.5}Ti_{1.0}Fe_{0.08}O_x$)

Repeat of Example 2, except that the fumed titania and the iron acetate were added in the beginning, a few minutes after the antimony oxide was added.

Example 5

Catalyst No. 17173-18 ($V_{1.0}Sb_{1.2}Sn_{0.5}Ti_{1.0}Fe_{0.08}O_x$)

This was an exact repeat of Example 2; however, just before the catalyst slurry started to thicken, 30% $H_2O_2$ was added to peptize the slurry.

Examples 6–9

General

In each of Examples 6 to 9, the same preparation method as described under Example 1 was followed, except that only half the amount of silica sol was added, making this first step catalyst precursor 75% active phase and 25% silica sol. The catalyst precursor was then dried and divided into four portions:

Catalyst No. 17173-59-A ($V_{1.0}Sb_{1.2}Sn_{0.5}Ti_{1.0}Fe_{0.08}O_x$): Dried at 120° C. for 16 hours only.

Catalyst No. 17173-59-B ($V_{1.0}Sb_{1.2}Sn_{0.5}Ti_{1.0}Fe_{0.08}O_x$): Dried at 120° C. for 16 hours, heat treated at 290° C. for 3 hours, at 425° C. for 3 hours.

Catalyst No. 17173-59-C ($V_{1.0}Sb_{1.2}Sn_{0.5}Ti_{1.0}Fe_{0.08}O_x$): Dried at 120° C. for 16 hours, heat treated at 290° C. for 3 hours, at 425° C. for 3 hours, at 650° C. for 8 hours.

Catalyst No. 17173-59-D ($V_{1.0}Sb_{1.2}Sn_{0.5}Ti_{1.0}Fe_{0.08}O_x$): Dried at 120° C. for 16 hours, heat treated at 290° C. for 3 hours, at 425° C. for 3 hours, at 650° C. for 8 hours, at 900° C. for 3 hours.

Each catalyst precursor described above was then combined with the second half of the silica sol to give a final composition of 60% active phase and 40% silica sol. The precursor was ball-milled with the silica sol for ~2 hours, was then evaporated on a hot plate, and dried at 120° C. overnight. The catalyst was calcined at 290° C. for 3 hours, 425° C. for 3 hours, 650° C. for 8 hours, was ground and screened to a 20 to 35 mesh size. The catalyst was then calcined further at 900° C. for 3 hours.

Example 6

Catalyst No. 17173-63

17173-59-A was combined with silica sol and treated as described above.

Example 7

Catalyst No. 17173-68

17173-59-B was combined with silica sol and treated as described above.

Example 8

Catalyst No. 17173-84

17173-59-C was combined with silica sol and treated as described above. After the final heat-treatment, the catalyst was washed in methanol and post-calcined at 650° C. for 3 hours.

Example 9

Catalyst No. 17173-90

17173-59-D was combined with silica sol and treated as described above. After the final heat-treatment, the catalyst was washed in methanol and post-calcined at 650° C. for 3 hours.

Comparative Examples 10 to 13

General

In each of examples 10–13, the same preparation method as described under Example 1 was used, except no silica sol was added, making this first step catalyst precursor 100% active phase. This catalyst precursor was dried and then divided into four portions:

Catalyst No. 17173-58-A ($V_{1.0}Sb_{1.2}Sn_{0.5}Ti_{1.0}Fe_{0.08}O_x$): Dried at 120° C. for 16 hours only.

Catalyst No. 17173-58-B ($V_{1.0}Sb_{1.2}Sn_{0.5}Ti_{1.0}Fe_{0.08}O_x$): Dried at 120° C. for 16 hours, heat treated at 290° C. for 3 hours, at 425° C. for 3 hours.

Catalyst No. 17173-58-C ($V_{1.0}Sb_{1.2}Sn_{0.5}Ti_{1.0}Fe_{0.08}O_x$): Dried at 120° C. for 16 hours, heat treated at 290° C. for 3 hours, at 425° C. for 3 hours, at 650° C. for 8 hours.

Catalyst No. 17173-58-D ($V_{1.0}Sb_{1.2}Sn_{0.5}Ti_{1.0}Fe_{0.08}O_x$): Dried at 120° C. for 16 hours, heat treated at 290° C. for 3 hours, at 425° C. for 3 hours, at 650° C. for 8 hours, at 900° C. for 3 hours.

Each catalyst precursor described above was then combined with the silica sol to give a final composition of 60% active phase and 40% silica sol. The precursor was ball-milled with the silica sol for ~2 hours, was then evaporated on a hot plate, and dried at 120° C. overnight. The catalyst was calcined at 290° C. for 3 hours, 425° C. for 3 hours, 650° C. for 8 hours, was ground and screened to a 20 to 35 mesh size. The catalyst was then calcined further at 900° C. for 3 hours, washed in methanol and post-calcined at 650° C. for 3 hours.

Example 10

Catalyst No. 17173-62

17173-58-A was combined with silica sol and treated as described above.

Example 11

Catalyst No. 17173-64

17173-58-B was combined with silica sol and treated as described above.

Example 12

Catalyst No. 17173-76

17173-58-C was combined with silica sol and treated as described above.

Example 13

Catalyst No. 17173-89

17173-58-D was combined with silica sol and treated as described above.

The results of the tests of the catalyst produced by the process of the present invention are set forth in Table I below.

What we claim as our invention is:

1. A process of preparing a supported catalyst wherein said catalyst comprises the elements and proportions indicated by the following empirical formula:

$$V_{1.0}Sb_aM_bO_x$$

wherein
M equals Sn, Ti, Fe, Cu, Nb, Ta, Co, Ni, Mg, Li, Na, Ga and mixtures thereof,
a is from about 0.5 to about 5.0,
b is from about 0.1 to 5.0, and
x is the number of oxygen atoms required to satisfy the valency requirement of the other elements,
comprising (1) mixing the vanadium compound, at least a portion of the antimony compound, and at least a portion of the M compound and an aqueous sol containing a portion of the support material to form an aqueous slurry, heating the slurry to remove the water, and calcining at a temperature of at least about 150° C. to form a catalyst precursor; (2) mixing the catalyst precursor with an aqueous sol containing the remaining portion of the support for the catalyst and any remaining portion of the Sb compound and M compound to form a second slurry; (3) drying the second slurry to remove the water to form a dry mixture; and (4) calcining the dried mixture at a temperature of at least 150° C. to form the finished catalyst.

2. The process of claim 1 wherein the portion of support material added during the formation of the catalyst precursor is between 1 to 79 percent of the total amount of support material present in the finished catalyst.

3. The process of claim 1 wherein the remaining portion of support material present in the aqueous sol to which the catalyst precursor is mixed is between 1 to 79 percent of the total amount of support material present in the finished catalyst.

TABLE I

| Ex. | Catalyst # | Description | Temp. of 1st Stg. Processing (° C.) | % Solids when Gelled | Viscosity (cps) | % 20–35 Mesh Size | Relative Hardness | % AN |
|---|---|---|---|---|---|---|---|---|
| Desirable Characteristics | | | | 35–45 | <1,000 | >42.5 | >1.0 | >77.0 |
| Comparative Examples | | | | | | | | |
| 1 | 17147-92B | Base: One-stg. prep. | | 24 | >1,000 | 42.5 | 1.0 (std.) | 80.3 |
| 2 | 17173-15 | Base: Repeat prep. | | | | | | 79.7 |
| 3 | 17173-16 | Base: Repeat prep. | | | | | | 79.5 |
| 4 | 17173-17 | Base: Repeat prep. | | | | | | 78.9 |
| 5 | 17173-18 | Base: Repeat prep. | | | | | | 80.4 |
| | | | | | | | Ave. = | 79.8 |
| Examples | | | | | | | | |
| 6 | 17173-63 | 1/2 SiO₂ added in 2nd stg. | 130 | 41 | <1,000 | 36.5 | 0.86 | 78.3 |
| 7 | 17173-68 | 1/2 SiO₂ added in 2nd stg. | 425 | | | 49.4 | 1.16 | 78.8 |
| 8 | 17173-84 | 1/2 SiO₂ added in 2nd stg. | 650 | | | 48.7 | 1.14 | 79.5 |
| 9 | 17173-90 | 1/2 SiO₂ added in 2nd stg. | 900 | | | 48.8 | 1.15 | 77.0 |
| Comparative Examples | | | | | | | | |
| 10 | 17173-62 | All SiO₂ added in 2nd stg. | 130 | 61 | <1,000 | 39.6 | 0.93 | 74.6 |
| 11 | 17173-64 | All SiO₂ added in 2nd stg. | 425 | | | 38.2 | 0.90 | 78.3 |
| 12 | 17173-76 | All SiO₂ added in 2nd stg. | 650 | | | 55.3 | 1.30 | |
| 13 | 17173-89 | All SiO₂ added in 2nd stg. | 900 | | | 41.8 | 0.98 | |

As will be evident to those skilled in the art, various modifications of this invention can be made or followed in light of the foregoing disclosure and discussion without departing from the spirit and scope of the disclosure or from the scope of the claims.

4. The process of claim 1 wherein all of the Sb compound is added during the formation of the catalyst precursor.

5. The process of claim 4 wherein all of the M compound is added during the formation of the catalyst precursor.

6. The process of claim 1 wherein the catalyst precursor is calcined to a temperature between about 150° to about 900° C.

7. The process of claim 6 wherein the catalyst precursor is calcined at a temperature of between about 300° to about 600° C.

8. The process of claim 2 wherein the catalyst precursor is calcined to a temperature between about 150° to about 900° C.

9. The process of claim 2 wherein the catalyst precursor is calcined at a temperature of between about 300° to about 600° C.

10. The process of claim 1 wherein the support material is selected from the group consisting of silica, alumina, titanium, zirconia and mixtures thereof.

11. The process of claim 2 wherein the support material is selected from the group consisting of silica, alumina, titanium, zirconia and mixtures thereof.

12. The process of claim 3 wherein the support material is selected from the group consisting of silica, alumina, titanium, zirconia and mixtures thereof.

13. The process of claim 1 further comprising mixing during the formation of the catalyst precursor an aqueous dispersion containing the vanadium compound and at least a portion of the Sb compound while the vanadium is in solution.

* * * * *

UNITED STATES PATENT AND TRADEMARK OFFICE
CERTIFICATE OF CORRECTION

PATENT NO. : 6,451,730 B1
DATED : September 17, 2002
INVENTOR(S) : Maria Strada Friedrich, Michael J. Seely and Dev Dhanaraj Suresh It is certified that error appears in the above-identified patent and that said Letters Patent is hereby corrected as shown below:

<u>Column 4,</u>
Lines 6 and 7, "invention, Support material is" should read -- invention, the support material is"
Line 8, "silica, alumina titanium," should read -- silica, alumina, titanium,"
Line 22, "V1.0Sb$_a$M$_b$0$_x$" should read -- V$_{1.0}$Sb$_a$M$_b$0$_x$ --

Signed and Sealed this

Fourteenth Day of January, 2003

JAMES E. ROGAN
*Director of the United States Patent and Trademark Office*